(12) United States Patent
Stack et al.

(10) Patent No.: US 6,592,616 B1
(45) Date of Patent: Jul. 15, 2003

(54) SYSTEM AND DEVICE FOR MINIMIZING EMBOLIC RISK DURING AN INTERVENTIONAL PROCEDURE

(75) Inventors: Richard S. Stack, Chapel Hill, NC (US); Paul F. Muller, San Carlos, CA (US); Udayan G. Patel, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/560,209

(22) Filed: Apr. 28, 2000

(51) Int. Cl.[7] .................................................. A61F 2/06
(52) U.S. Cl. ...................................... 623/1.17; 623/1.23
(58) Field of Search .............................. 623/1.15, 1.11, 623/1.1–1.23; 600/200, 108, 194; 604/508, 509, 510, 96.01, 103.05

(56) References Cited

U.S. PATENT DOCUMENTS

| | | | |
|---|---|---|---|
| 3,952,747 A | | 4/1976 | Kimmell, Jr. |
| 4,355,426 A | * | 10/1982 | MacGregor ................ 623/1.32 |
| 4,425,908 A | | 1/1984 | Simon |
| 4,494,531 A | | 1/1985 | Gianturco |
| 4,612,931 A | | 9/1986 | Dormia |
| 4,619,246 A | | 10/1986 | Molgaard-Nielsen et al. |
| 4,643,184 A | | 2/1987 | Mobin-Uddin |
| 4,650,466 A | | 3/1987 | Luther |
| 4,662,885 A | | 5/1987 | DiPisa, Jr. |
| 4,688,553 A | | 8/1987 | Metals |
| 4,706,671 A | | 11/1987 | Weinrib |
| 4,723,549 A | | 2/1988 | Wholey et al. |
| 4,727,873 A | | 3/1988 | Mobin-Uddin |
| 4,781,177 A | | 11/1988 | Lebigot |
| 4,790,812 A | | 12/1988 | Hawkins, Jr. et al. |
| 4,790,813 A | | 12/1988 | Kensey |
| 4,794,928 A | | 1/1989 | Kletschka |
| 4,832,055 A | | 5/1989 | Palestrant |
| 4,873,978 A | | 10/1989 | Ginsburg |
| 4,921,478 A | | 5/1990 | Solano et al. |
| 4,921,484 A | | 5/1990 | Hillstead |
| 4,969,891 A | | 11/1990 | Gewertz |
| 4,990,156 A | | 2/1991 | Lefebvre |
| 4,997,435 A | | 3/1991 | Demeter |
| 4,998,539 A | | 3/1991 | Delsanti |
| 5,053,008 A | | 10/1991 | Bajaj |
| 5,064,428 A | | 11/1991 | Cope et al. |
| 5,071,407 A | | 12/1991 | Termin et al. |
| 5,092,839 A | | 3/1992 | Kipperman |
| 5,100,425 A | | 3/1992 | Fischell et al. |
| 5,102,415 A | | 4/1992 | Guenther et al. |

(List continued on next page.)

FOREIGN PATENT DOCUMENTS

| | | |
|---|---|---|
| EP | 0 427 429 A2 | 5/1991 |
| EP | 0 472 334 A1 | 2/1992 |
| EP | 0 809 980 A2 | 12/1997 |
| FR | 2 714 816 | 7/1995 |
| WO | WO92/03097 | 3/1992 |
| WO | WO96/01591 | 1/1996 |
| WO | WO 96/14808 | 5/1996 |
| WO | WO97/17100 | 5/1997 |
| WO | WO99/23976 | 5/1999 |

*Primary Examiner*—Michael J. Milano
*Assistant Examiner*—(Jackie) Tan-Uyen T. Ho
(74) *Attorney, Agent, or Firm*—Fulwider Patton Lee & Utecht, LLP (57) ABSTRACT

A device for trapping plaque against the vascular wall includes a tubular-shaped net which is made from a blood-permeable and biocompatible material having expandable members attached to each end of the tubular net. The expandable members are placed in their expanded position within a blood vessel to maintain the tubular net against the area of plaque to be treated with an interventional procedure. A balloon angioplasty procedure or stenting procedure is subsequently performed within the inner lumen formed in the tubular net. The tubular net prevents any emboli which may be created during the interventional procedure from entering into the bloodstream.

6 Claims, 8 Drawing Sheets

U.S. PATENT DOCUMENTS

| | | | |
|---|---|---|---|
| 5,108,419 A | 4/1992 | Reger et al. | |
| 5,152,777 A | 10/1992 | Goldberg et al. | |
| 5,160,342 A | 11/1992 | Reger et al. | |
| 5,192,286 A | 3/1993 | Phan et al. | |
| 5,324,304 A | 6/1994 | Rasmussen | |
| 5,329,942 A | 7/1994 | Gunther et al. | |
| 5,330,482 A | 7/1994 | Gibbs et al. | |
| 5,350,398 A | 9/1994 | Pavcnik et al. | |
| 5,370,657 A | 12/1994 | Irie | |
| 5,383,887 A | 1/1995 | Nadal | |
| 5,421,832 A | 6/1995 | Lefebvre | |
| 5,458,615 A * | 10/1995 | Klemm et al. | 604/103.04 |
| 5,490,859 A | 2/1996 | Mische et al. | |
| 5,496,277 A | 3/1996 | Termin et al. | |
| 5,496,330 A | 3/1996 | Bates et al. | |
| 5,501,694 A | 3/1996 | Ressemann et al. | |
| 5,549,626 A | 8/1996 | Miller et al. | |
| 5,591,229 A * | 1/1997 | Parodi | 606/195 |
| 5,601,595 A | 2/1997 | Smith | |
| 5,626,605 A | 5/1997 | Irie et al. | |
| 5,634,942 A | 6/1997 | Chevillon et al. | |
| 5,649,953 A | 7/1997 | Lefebvre | |
| 5,662,671 A | 9/1997 | Barbut et al. | |
| 5,669,933 A | 9/1997 | Simon et al. | |
| 5,681,347 A | 10/1997 | Cathcart et al. | |
| 5,695,518 A | 12/1997 | Laerum | |
| 5,695,519 A | 12/1997 | Summers et al. | |
| 5,720,764 A | 2/1998 | Naderlinger | |
| 5,725,550 A | 3/1998 | Nadal | |
| 5,728,131 A * | 3/1998 | Frantzen et al. | 606/191 |
| 5,746,767 A | 5/1998 | Smith | |
| 5,755,790 A | 5/1998 | Chevillon et al. | |
| 5,769,816 A | 6/1998 | Barbut et al. | |
| 5,769,887 A * | 6/1998 | Brown et al. | 606/194 |
| 5,772,674 A | 6/1998 | Nakhjavan | |
| 5,779,716 A | 7/1998 | Cano et al. | |
| 5,792,145 A | 8/1998 | Bates et al. | |
| 5,792,156 A | 8/1998 | Perouse | |
| 5,792,157 A | 8/1998 | Mische et al. | |
| 5,795,322 A | 8/1998 | Boudewijn | |
| 5,800,457 A | 9/1998 | Gelbfish | |
| 5,800,525 A | 9/1998 | Bachinski et al. | |
| 5,810,874 A | 9/1998 | Lefebvre | |
| 5,814,064 A | 9/1998 | Daniel et al. | |
| 5,827,324 A | 10/1998 | Cassell et al. | |
| 5,833,650 A | 11/1998 | Imran | |
| 5,836,868 A | 11/1998 | Ressemann et al. | |
| 5,846,251 A | 12/1998 | Hart | |
| 5,846,260 A | 12/1998 | Maahs | |
| 5,848,964 A | 12/1998 | Samuels | |
| 5,868,708 A | 2/1999 | Hart et al. | |
| 5,876,367 A | 3/1999 | Kaganov et al. | |
| 5,879,380 A | 3/1999 | Kalmann et al. | |
| 5,897,567 A | 4/1999 | Ressemann et al. | |
| 5,910,154 A | 6/1999 | Tsugita et al. | |
| 5,911,734 A | 6/1999 | Tsugita et al. | |
| 5,941,896 A | 8/1999 | Kerr | |
| 5,948,191 A | 9/1999 | Solovay | |
| 5,968,071 A | 10/1999 | Chevillon et al. | |
| 5,976,172 A | 11/1999 | Homsma et al. | |
| 5,980,555 A | 11/1999 | Barbut et al. | |
| 5,989,281 A | 11/1999 | Barbut et al. | |
| 6,001,118 A | 12/1999 | Daniel et al. | |
| 6,013,093 A | 1/2000 | Nott et al. | |
| 6,152,956 A * | 11/2000 | Pierce | 604/215 |
| 6,319,278 B1 * | 11/2001 | Quinn | 623/1.13 |
| 6,355,056 B1 * | 3/2002 | Pinheiro | 623/1.13 |
| 6,383,171 B1 | 5/2002 | Gifford et al. | |

\* cited by examiner

SYSTEM AND DEVICE FOR MINIMIZING EMBOLIC RISK DURING AN INTERVENTIONAL PROCEDURE

BACKGROUND OF THE INVENTION

The present invention relates to angioplasty procedures, and more particularly, to a system and device for preventing arterial plaque from dislodging from the arterial wall during procedures such as, for example, percutaneous transluminal coronary angioplasty (PTCA) or percutaneous transluminal angioplasty (PTA), especially carotid PTA, and entering into the bloodstream where the embolic debris can occlude the flow of oxygenated blood to vital organs, such as the brain, which can cause devastating consequences to the patient. The present invention also relates to methods for using such a system and device.

In typical carotid PTA procedures, a guiding catheter or sheath is percutaneously introduced into the cardiovascular system of a patient through the femoral arteries and advanced through the vasculature until the distal end of the guiding catheter is in the common carotid artery. A guidewire and a dilatation catheter having a balloon on the distal end are introduced through the guiding catheter with the guidewire sliding within the dilatation catheter. The guidewire is first advanced out of the guiding catheter into the patient's carotid vasculature and is directed across the arterial lesion. The dilatation catheter is subsequently advanced over the previously advanced guidewire until the dilatation balloon is properly positioned across the arterial lesion. Once in position across the lesion, the expandable balloon is inflated to a predetermined size with a radiopaque liquid at relatively high pressure to radially compress the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

In angioplasty procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. Stents are usually delivered in a compressed condition to the target location and then are deployed into an expanded condition to support the vessel and help maintain it in an open position. The stent is usually crimped tightly onto a delivery catheter and transported in its delivery diameter through the patient's vasculature. The stent is expandable upon application of a controlled force, often through the inflation of the balloon portion of the delivery catheter, which expands the compressed stent to a larger diameter to be left in place within the artery at the target location. The stent also may be of the self-expanding type formed from, for example, shape memory metals or super-elastic nickel-titanium (NiTi) alloys, which will automatically expand from a compressed state when the stent is advanced out of the distal end of the delivery catheter into the body lumen.

The above non-surgical interventional procedures, when successful, avoid the necessity for major surgical operations. However, a danger which is always present during these procedures is the potential for particles of the atherosclerotic plaque, which can be extremely friable, breaking away from the arterial wall. For example, during deployment of a stent, the metal struts of the stent can possibly cut into the stenosis and shear off pieces of plaque which become embolic debris that will travel downstream and lodge somewhere in the patient's vascular system. Pieces of plaque material can sometimes dislodge from the stenosis during a balloon angioplasty procedure and become released into the bloodstream. When any of the above-described procedures are performed in the carotid arteries, the release of emboli into the circulatory system can be extremely dangerous and sometimes fatal to the patient. Debris that is carried by the bloodstream to distal vessels of the brain can cause these cerebral vessels to occlude, resulting in a stroke, and in some cases, death. Therefore, although cerebral percutaneous transluminal angioplasty has been performed in the past, the number of procedures performed has been limited due to the justifiable fear of causing an embolic stroke should embolic debris enter the bloodstream and block vital downstream blood passages.

Medical devices have been developed to attempt to deal with the problem created when debris or fragments enter the circulatory system following treatment utilizing the above-identified procedures. Some techniques which have had limited success include the placement of a filter or trap downstream from the treatment site to capture embolic debris before it reaches the smaller blood vessels downstream. However, there have been problems associated with filtering systems, particularly during the expansion and collapsing of the filter within the body vessel. If the filtering device does not have a suitable mechanism for closing the filter, there is a possibility that trapped embolic debris can backflow through the open end of the filter and enter the blood-stream as the filtering system is being collapsed for removal from the patient. In such a case, the act of collapsing the filter device may actually squeeze trapped embolic material through the opening of the filter. In other instances, the rate of blood percolating through the filtering material may be slower than the normal blood flow which can either cause the filtering material to tear or cause the filter to dislodge from the deployed position due to the build up of fluid pressure behind the filter. Moreover, should the filter become clogged with debris, there is a possibility that blood circulation past the clogged filter will be insufficient for the downstream vessels. If a filter should become clogged when in use in the carotid arteries, blood flow could be diminished to the vessels leading to the brain. While the brain may be capable of functioning for a short period of time without sufficient blood flow, blood stoppage of more than thirty to forty seconds could cause the patient to experience a seizure. If the physician administering the procedure is unaware that the filtering device is clogged and that there is little or no blood flowing to the brain, the injury to the patient can be as devastating as if an emboli itself had caused blockage of the cerebral arteries.

In light of the above, it becomes apparent that there remains a need for a device or method that will prevent friable plaque from breaking away from arterial walls during intravascular procedures and forming emboli in the bloodstream, which is easy and safe to deploy, and that may be implanted for extended periods of time with minimal adverse impact or immunological response to the patient. Such a system or device would be advantageous if it prevents the need to catch and remove embolic material in the bloodstream by preventing such an occurrence in the first place. The inventions disclosed herein satisfy these and other needs.

SUMMARY OF THE INVENTION

The present invention provides a system and device for trapping embolic debris which may be created during the performance of a therapeutic interventional procedure, such as a balloon angioplasty or stenting procedure, to prevent the emboli from entering into the bloodstream and lodging and blocking blood vessels downstream from the interventional site. The present invention is particularly useful while performing an interventional procedure in critical arteries, such as the carotid arteries, in which downstream blood vessels can become blocked with embolic debris, including the main blood vessels leading to the brain or other vital organs. The present invention is particularly advantageous since any embolic debris which may be created during the interventional procedure is never actually released into the bloodstream, eliminating the need to deploy a filtering device to catch and remove debris in the bloodstream, the task performed by many prior art blood filters and embolic catching systems. Rather, the present invention employs the use of a "safety net" or filter which traps the plaque against the vascular wall where the stenosis is located, basically "encapsulating" the area to be treated to prevent any embolic debris from entering the bloodstream in the first place. As a result, a physician will have a high degree of confidence that any embolic debris which may be created during the interventional procedure will not enter the bloodstream since this "safety net" creates a barrier that prevents particles from being released into the bloodstream.

A filtering or plaque-trapping device for trapping plaque against a vascular wall made in accordance with the present invention may include a tubular shaped net which is made from a blood permeable and biocompatible material having expansion members attached to each end of the tubular net. The expansion members are expandable from a contracted or collapsed position to an expanded position to contact the wall of the blood vessel to maintain the tubular netting affixed against the wall of the blood vessel where the area of plaque or stenosis is located. This plaque-trapping device "encapsulates" the area of plaque with a fine meshing that filters or prevents embolic material from being released into the bloodstream.

Each expandable member can be made from a single expandable ring which can be deployed utilizing a delivery catheter made in accordance with the present invention. In another embodiment of the invention, the expandable ring can be made from a self-expanding material such as Nitinol (NiTi) alloy which allows the expandable rings to self-expand to contact the wall of the vessel and maintain the tubular netting in place over the area of plaque. Alternatively, the expandable rings could also be made from a material which can be expanded through the use of a controlled force, such as the inflation of a balloon, which allows the physician to deploy the device over the area of plaque before the interventional procedure starts. Once the plaque-trapping device is in place, the physician can treat the area of plaque utilizing balloon angioplasty techniques or stenting procedures which will compress the plaque build-up and enlarge the diameter of the blood vessel to allow greater blood flow through that region. Regardless of whether a balloon angioplasty procedure or stenting procedure is performed, the plaque-trapping device remains permanently implanted within the patient since the device is made from a blood permeable and biocompatible material. Thus, the tubular net provides a means for encapsulating the compressed area thus preventing the release of any created emboli into the bloodstream.

In one embodiment of the invention, at least one strut is attached to each end ring of the device to help maintain a set longitudinal length for the plaque trapping device and help maintain the expandable members in proper alignment. As a result, during deployment of the device, there is less chance that the tubular net would be improperly positioned in the area of treatment, resulting in the full length of the tubular net being maintained over the area of plaque build-up. Thereafter, a larger primary stent can be placed through the internal lumen of the tubular net to crush the plaque build-up and increase the diameter of the blood vessel.

Since the plaque-trapping device remains within the patient's vasculature, it is possible to use a primary stent with the present invention which can be designed with larger "cells" or wider gaps between the struts of the stent. As a result, the primary stent can be made much more flexible and will be more easily maneuverable through the patient's vasculature allowing the stent to be designed having a lower profile to enable the physician to reach tight, distal lesions. Also, since a flexible net is placed between the primary stent and the area of plaque, there is less possibility of the struts of the stent "digging" into the plaque to shear off pieces which can cause emboli. The present device reduces the risk of acute or long term stroke in carotid procedures, reduces risk of renal failure due to the release of embolic particles into the bloodstream during renal procedures, and reduces the risk of losing a limb or a portion of the limb caused by the blockage of a vital artery in peripheral vascular procedures.

In another embodiment of the present invention, the expandable members located at the end of the tubular net portion may be stents which can either be selfexpanding or deployable by balloon inflation or other expansion means. The use of stents at the ends of the tubular net allows for secure placement of the device within the vasculature of the patient. Once the device is in place, balloon angioplasty can be performed or, alternatively, a stenting procedure can be performed to crush the plaque and maintain the blood vessel in an open position.

The present invention is also directed to a delivery catheter which provides a two-stage deployment of both the plaque trapping device and the primary stent used in the interventional procedure. The delivery catheter includes an inner member having a mounting region which allows the primary stent to be mounted thereon, along with a second mounting region utilized for mounting the plaque-trapping device. In one particular embodiment of the present invention, the mounting region for the plaque-trapping device is distal to, and has a smaller diameter than, the mounting region for the primary stent to allow greater ease in crossing highly stenosed regions of a blood vessel. As a result, the plaque-trapping device can be placed immediately into the area of treatment to provide the physician with a high level of comfort knowing that as the larger portion of the delivery catheter is being positioned through the stenosis, any inadvertent crushing of the plaque which could create embolic debris will be immediately trapped by the plaque-trapping device. Again, the plaque-trapping device and delivery catheter provides the physician with a higher level of confidence when performing high-risk interventional procedures since the plaque-trapping device provides a virtual fail-safe system and method for preventing the release of embolic debris into the bloodstream.

Other features and advantages of the present invention will become more apparent from the following detailed description of the preferred embodiments of the invention, when taken in conjunction with the accompanying exemplary drawings.

DETAILED DESCRIPTION OF THE PREFERRED EMBODIMENTS

The present invention is directed to a system and device for minimizing embolic risk during the interventional procedure which helps prevent the release of any embolic debris created during an interventional procedure from being released into the bloodstream where the debris can lodge in critical arteries, cutting off blood flow to vital organs. While the present invention is described in detail as applied to the carotid artery of the patient, and the disclosed interventional procedure is directed to a stenting procedure, those skilled in the art will appreciate that it can also be used in other body lumens as well, such as the coronary arteries, renal arteries, saphenous veins and other peripheral arteries. Additionally, the present invention can be utilized while performing other interventional procedures, such as a balloon angioplasty procedure.

Figure 1:
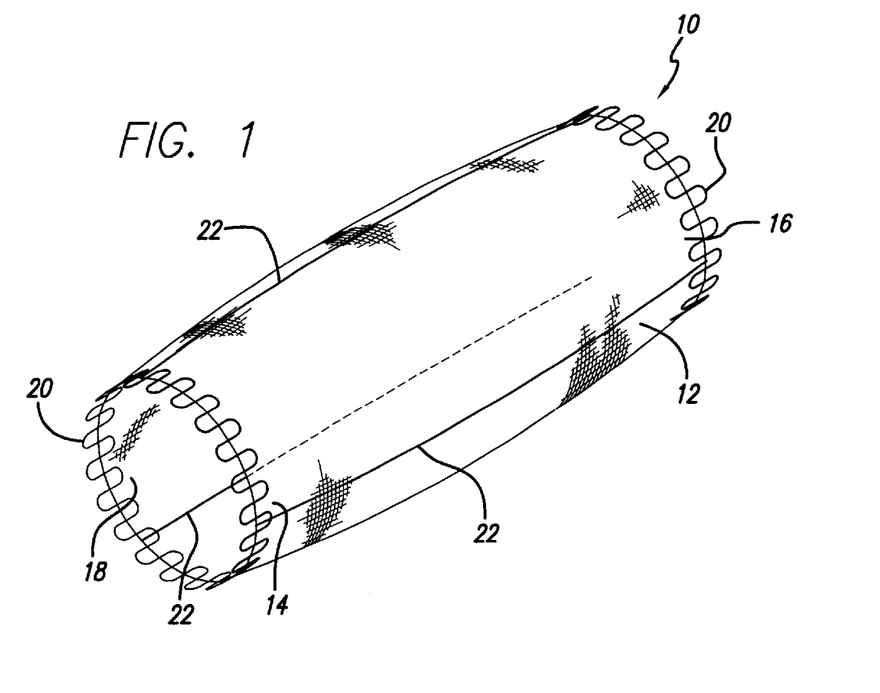
FIG. 1 is a perspective view of one particular embodiment of a plaque-trapping device made in accordance with the present invention.

FIG. 1 illustrates a plaque-trapping device 10 incorporating features of the present invention. In the particular embodiments shown in FIG. 1, the plaque-trapping device 10 comprises of a tubular net 12 with a proximal end 14 and a distal end 16, and defining an inner lumen 18 extending there between. An expandable member 20, which is shown in this particular embodiment as an expandable end ring, is attached to the proximal end 14 and distal end 16. The expandable member 20 also could be manufactured as an expandable arc (i.e., a portion of a ring) which opens the tubular net 12 once expanded. A longitudinal strut 22 is attached to each of the expandable members 20 located at the distal end 16 and proximal end 14 of the tubular net 12. As shown in FIG. 1, there are actually three or four longitudinal struts 22 attached to the expandable members 20 in this particular embodiment. More or less longitudinal struts can be implemented as well. Additionally, more expandable members 20 could also be spaced along the length of the tubular net 12, if desired. These longitudinal struts 22 are circumferentially positioned 120 or 90 degrees apart and help maintain a set longitudinal length between the expandable members 20 to maintain the entire length of the tubular net 12 in place over the area of plaque once deployed into the patient's vasculature. These longitudinal struts 22 also help maintain the expandable members 20 in proper alignment when deployed. These expandable members 20 are designed to expand radially outward from a contracted to an expanded position and contact the arterial wall to maintain the tubular net 12 in place after deployment. The plaque-trapping device 10, as depicted in FIG. 1, is shown in its expanded configuration.

Figure 2:
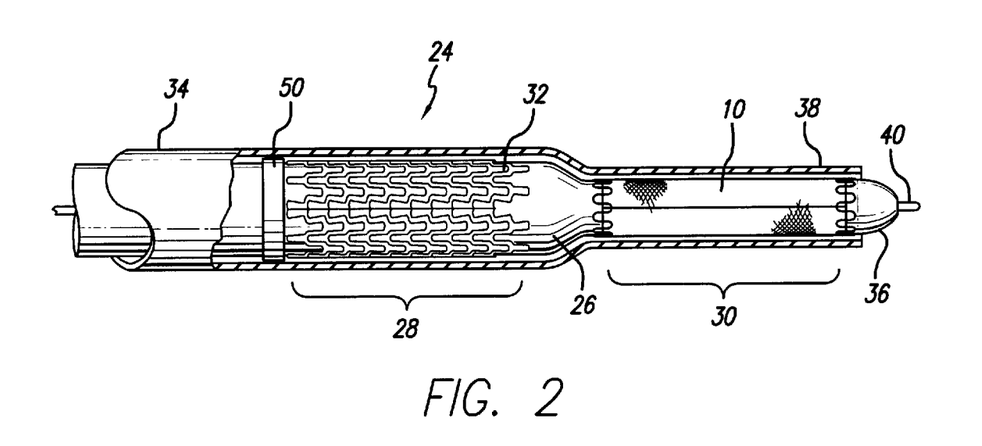
FIG. 2 is a side view, partially in section, of the end of a delivery catheter made in accordance with the present invention which shows the first mounting region for mounting the primary stent and a second mounting region for mounting a plaque-trapping device, such as the one shown in FIG. 1.

FIG. 2 illustrates a delivery catheter 24 also incorporating features of the present invention. In the particular embodiment shown in FIG. 2, the delivery catheter 24 includes an inner member 26 which has a first mounting region 28 and a second mounting region 30 formed therein. This first mounting region 28 is utilized for mounting a primary stent 32 which is to be deployed within the area of treatment in the patient's vasculature. The second mounting region 30 is designed for mounting a plaque-trapping device 10, such as the one shown in FIG. 1. This inner member 26 functions much like a stent holder in that the stent 32 and the plaque-trapping device 10 are placed in their contracted or collapsed position ready for deployment into the patient's vasculature. A restraining sheath 34 extends over the inner member 26, along with the stent 32 and plaque-trapping device 10. This restraining sheath 34 is designed to move axially in a longitudinal direction to first deploy the plaque-trapping device 10 within the area of plaque to be treated and then to deliver and place the primary stent 32 into the area of treatment for performance of the interventional procedure. The restraining sheath 34 should be sufficiently elastic to allow the sheath 34 to expand over the larger diameter inner member 26. Alternatively, the end portion of the sheath 34 which covers the plaque-trapping device 10 may be made from a material which is more elastic than the rest of the catheter, but strong enough to restrain the plaque trapping device 10.

In the embodiment of the delivery catheter 24 shown in FIG. 2, the inner member 26 is an elongated tubular member having a distal end 36 and a proximal end (not shown) which extends and remains outside the patient's body. The distal end 36 can be formed into a semi-spherical nose cone which is atramatic to prevent injury to the wall of the blood vessel as the catheter moves within the patient's vasculature. Likewise, the restraining sheath 34 includes a distal end 38 along with a proximal end (not shown) which also extends outside the patient's body. The proximal ends of the inner member 26 and restraining sheath 34 allow the physician to move the restraining sheath 34 as needed in order to retract the distal end 38 when deploying the plaque-trapping device 10 and stent 32. As is shown in FIG. 2, a guidewire 40 can be utilized to move the delivery catheter 24 to the target area using well-known over-the-wire techniques. A guidewire lumen (not shown) extends through the inner member 26 out to the proximal end where the guidewire 40 can be manipulated into place by the physician.

Referring now to FIGS. 3–7, the delivery catheter 24 is shown as it is placed within the internal carotid artery or other blood vessel of the patient. This artery 42 is shown having an area of treatment 44 in which atherosclerotic plaque 46 has built up against the inside wall 48 to decrease the diameter of the artery 42. As a result, blood flow is diminished through this area. As will be discussed below, the primary stent 32 will be implanted in this area of treatment 44 to compress the build-up of plaque 46 against the inside wall 48 to increase the diameter of the occluded area and help restore a sufficient supply of blood flow to downstream vessels. The stent 32 will not only help increase the diameter of the occluded area, but may also help prevent restenosis in the area of treatment 44.

Figure 3:
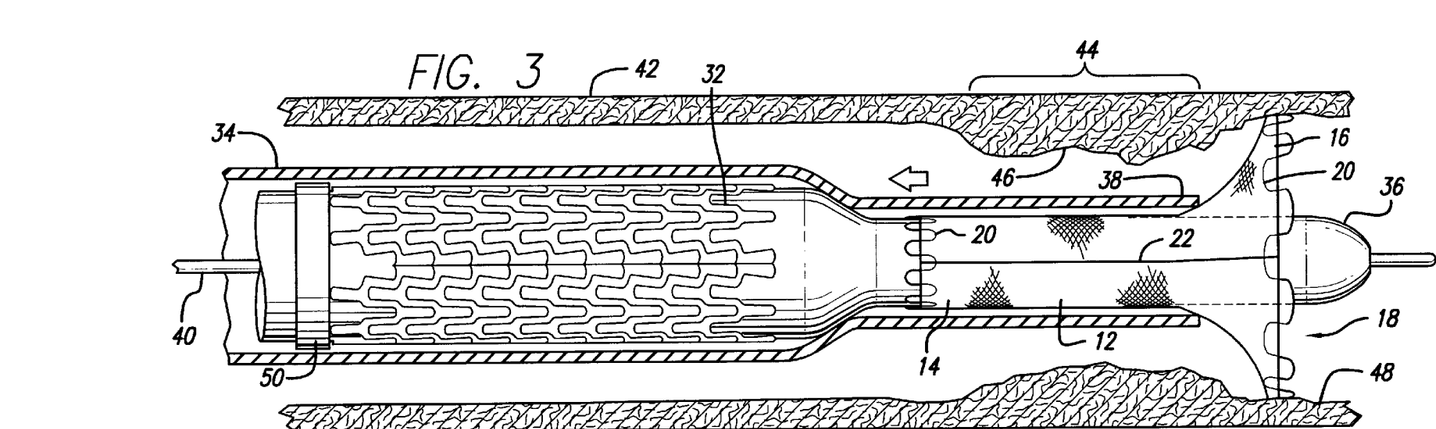
FIG. 3 is a cross-sectional view, partially in section, depicting the delivery catheter of the present invention disposed within a blood vessel of the patient wherein the plaque-trapping device is partially expanded within the vessel.

Referring now specifically to FIG. 3, the delivery catheter 24 is shown as its distal end 36 extends through the area of treatment 44 for the purpose of deploying the plaque-trapping device 10. As can be seen in FIG. 3, the distal end 16 of the plaque-trapping device 10 is initially deployed as the restraining sheath 34 is retracted to uncover the device 10. This allows the expandable member 20, which is attached to the distal end 16, to self-expand and come in contact with the inside wall 48 of the artery 42. It should be noted that in this particular embodiment shown in FIGS. 3–7, the expandable members 20 and the stent 32 are made from self-expanding materials which do not need an external force to expand the respective devices into their expanded condition. Rather, once the restraining sheath 34 is retracted, the restraining force which holds the device in its contracted position is removed, thus allowing the device to expand fully.

As can be seen in FIG. 3, the second mounting region 30 which is utilized to mount the plaque-trapping device 10 has a diameter or width which is smaller than the diameter of the first mounting region 28 which serves to hold the contracted stent 32 prior to deployment. This is due to the fact that the wall thickness of the tubular net can be as small as 0.003 inches, depending on the meshing material selected to form the net. This low profile of the second mounting region 30 allows the physician to easily cross the stenosis at the area of treatment 44 without causing plaque to break free and enter the bloodstream. In this manner, the physician utilizing a delivery catheter 24 made in accordance with the present invention can introduce the low profile plaque-trapping device 10 through highly built up occlusions in the artery without the fear of inadvertently breaking off pieces of plaque for release into the bloodstream. Later, when the larger diameter first mounting region crosses the stenosis, there is always a possibility that the larger sized catheter could place pressure in the area of treatment and cause pieces of plaque to break off before the stent is even deployed. Should this occur, the plaque-trapping device 10 is already in place to "encapsulate" the plaque 46 and prevent any particles from entering the bloodstream.

Figure 4:
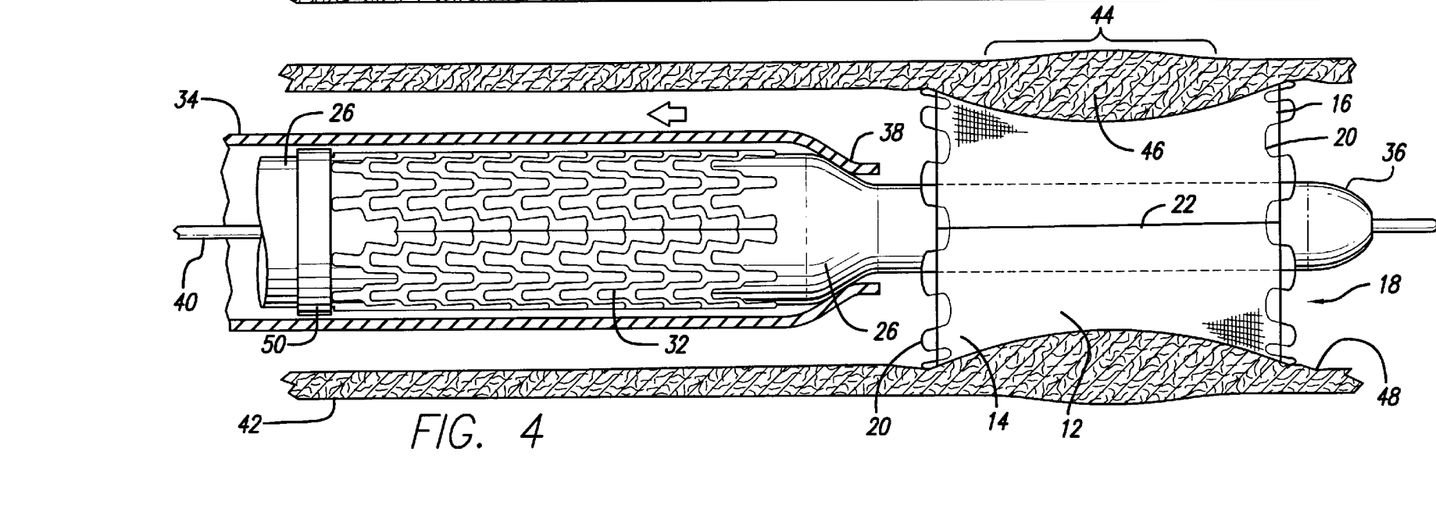
FIG. 4 is a cross-sectional view, partially in section, depicting the delivery catheter of the present invention disposed within a blood vessel of the patient wherein the plaque-trapping device is fully expanded against the atherosclerotic plaque site within the vessel.

Referring now to FIG. 4, the restraining sheath 34 is shown as it is further retracted to deploy the entire plaque-trapping device 10 into the area of treatment 44. As can be seen, the proximal end 14 of the device 10 is also deployed since the expandable member 20 expands to contact the inside walls 48 of the artery 42. The longitudinal struts 22 attached to each of the expandable members 20 help to maintain a predetermined length between the expandable members 20 so that the entire area of treatment 44 makes contact with the tubular net 12. Additionally, these longitudinal struts 22 serve to prevent the distal end 16 from being pulled back as the restraining sheath 34 is being retracted. Otherwise, there is a possibility that the distal end 16 would also move backward with the sheath as the sheath is retracted and an improper positioning of the device 10 over the area of treatment 14 could occur. As is shown in FIG. 4, the restraining sheath 34 remains in contact with the primary stent 32 preventing it from being deployed until the entire assembly is moved into the area of treatment by the physician.

Figure 5:
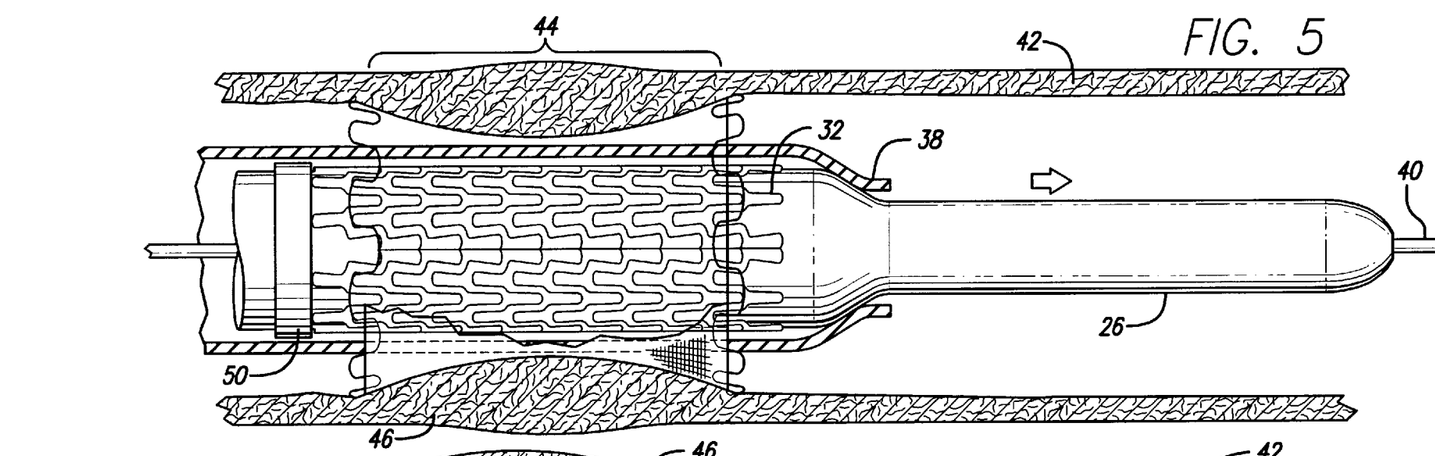
FIG. 5 is a side view, partially fragmented and in cross-section, of the delivery catheter shown in FIGS. 3–4, with the primary stent being positioned into the atherosclerotic plaque site in the vessel.

Referring now to FIG. 5, the delivery catheter 24 is shown moved forward so that the first mounting region with the retracted stent 32 is positioned in the area of treatment 44. This step is achieved by simply moving the delivery catheter 24 forward along the guidewire 40. As can be seen in FIG. 5, the first mounting region 28 and stent 32 extend within the inner lumen 18 of the plaque-trapping device 10. It should be noted that a radiopaque marker 50, made from a radiopaque material such as tantalum, is affixed on the inner member 26 to aid the physician in positioning the catheter with the aid of fluoroscopy. Once the delivery catheter is in place with the primary stent 32 aligned in the area of treatment, the restraining sheath 34 can be further retracted to deploy the stent into the area of treatment 44. This marker 50 also provides a shoulder region against which the proximal end of the stent can abut when the restraining sheath is retracted so that the stent is not retracted with the sheath 34.

Figure 6:
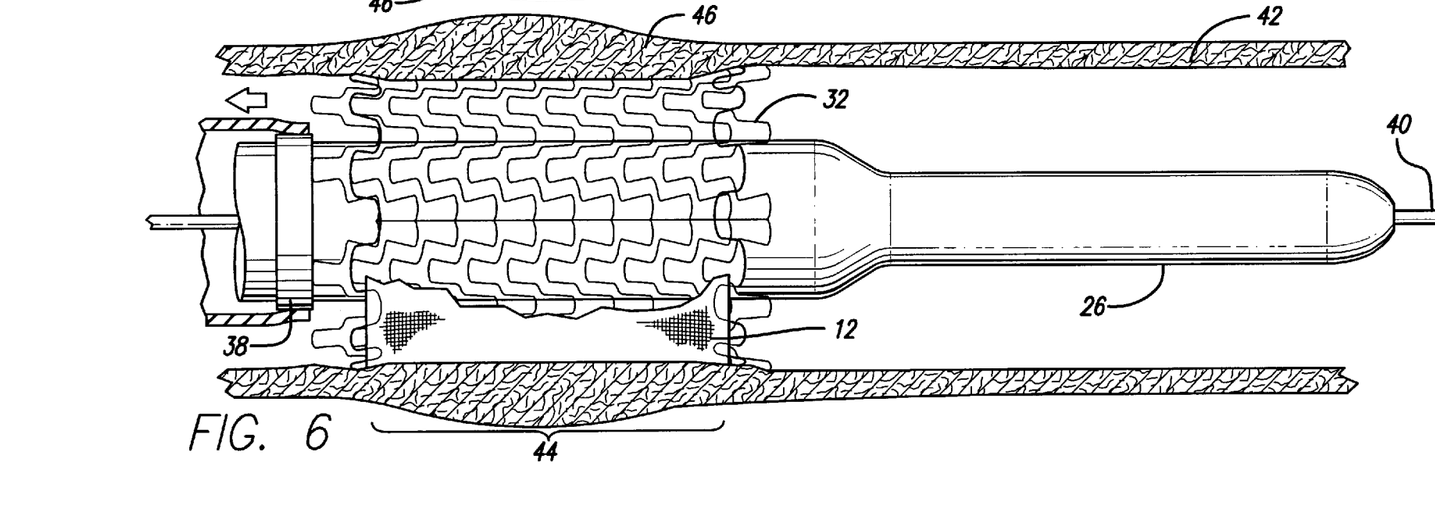
FIG. 6 is a side view, partially fragmented and in cross-section, of the delivery catheter with the primary stent in its expanded configuration compressing the plaque in the atherosclerotic plaque site in the vessel.

Referring now to FIG. 6, the restraining sheath 34 is shown as it is further retracted via the manipulation of the proximal end of the sheath by the physician. This allows the self-expanding stent 32 to move into its expanded condition which results in the plaque 46 in the area of treatment 44 being compressed to enlarge the diameter of the artery 42 and improve blood flow through this region. Again, since the particular embodiment of the delivery catheter 24 utilizes self-expandable members 20, the retraction of the restraining sheath releases the restraining force which holds the devices in place to allow for easy deployment.

Figure 7:
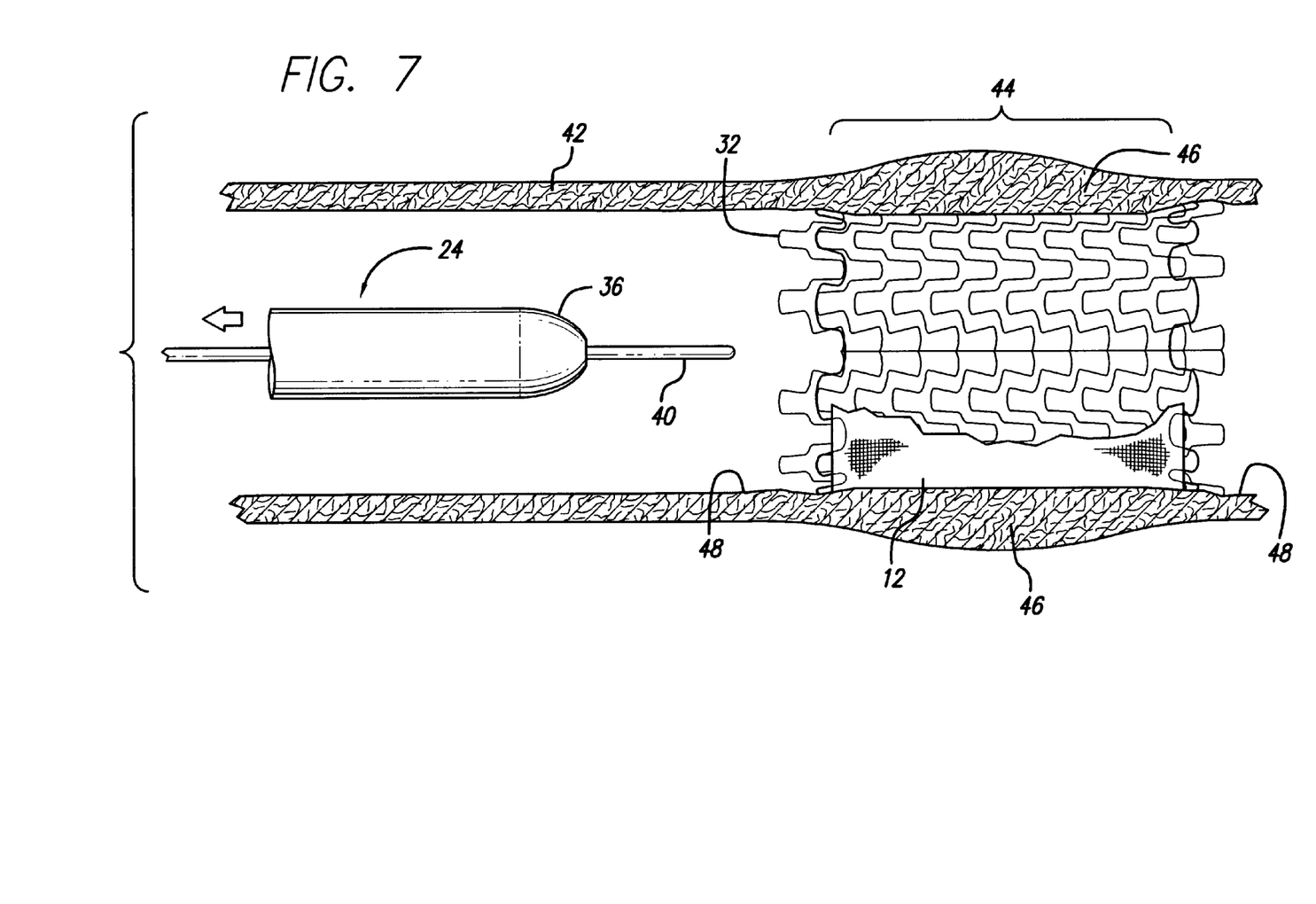
FIG. 7 is a side view, partially fragmented, of the plaque-trapping device in position against the atherosclerotic plaque site with the primary stent compressing the plaque to increase the diameter of the blood vessel.

Referring now to FIG. 7, the delivery catheter 24 is removed from the patient's vasculature and the resulting interventional procedure opens up the stenosed region of the artery 42. As a result of using the plaque-trapping device 10 in conjunction with the primary stent 43, any pieces of plaque which may have broken off the stenosis created during the interventional procedure are trapped between the inside wall 48 of the artery 42 and the tubular net 12. Since the tubular net 12 is made from a blood-permeable and biocompatible material, it remains implanted within the patient's vasculature along with the primary stent 32. It should be appreciated that although a stenting procedure is disclosed, it is also possible to place the plaque-trapping device 10 into the area of treatment 44 and then perform a balloon angioplasty with the device 10 in place. This, too, will cause the plaque 46 to compress and increase the diameter of the artery 42 in this region. Thereafter, a stent could also be placed in the enlarged area to help hold the artery in an open position once the balloon angioplasty procedure has been performed.

The tubular net 12 can comprise a mono-filament mesh having openings large enough to permit blood to pass freely through the mesh, but sufficiently small to filter out plaque fragments that may cause an embolism. For example, the openings in the tubular net can be small enough to filter emboli as small as 20 microns. Alternatively, the tubular net can be constructed of either a woven fabric, injection molded plastic, non-woven porous plastic, woven fibers of glass coated with polymeric materials, and other suitable filtering materials. The tubular net can also be made from, for example, nylon, porous PTFE, Dacron, or Gortex, manufactured by the Gore Co., and other similar, suitable materials. The tubular net should be flexible enough to allow the primary stent to properly compress the plaque in the area of treatment. Typically, the wall thickness of the tubular net can be as small as 0.003 inches to provide a smaller profile device when placed in the collapsed position.

The expandable members 20 are attached to the tubular net 12 utilizing sutures or any suitable adhesive which will bond at least a portion of the expandable member to the tubular net 12. Alternatively, a sleeve or pocket could be created on the tubular net 12 which could be utilized to house the expandable members 20. It should be appreciated that any suitable means for attaching the expandable members 20 to the tubular netting can be utilized without departing from the spirit and scope of the present invention. Additionally, the longitudinal struts 22 which are attached to each of the expandable members can be permanently affixed utilizing adhesives or welding techniques, depending upon the type of material selected for the struts 22 and the expandable members 20. It is also possible to suture or attach the length of the strut 22 to the tubular net 12 so that the longitudinal struts help hold the tubular net open once the device is deployed in the patient's vasculature. These longitudinal struts 22 can be made from conventional materials utilized in stent designs, such as stainless steel, tantalum, platinum, nitinol and the like. Additionally, the location of the expandable members and the longitudinal struts 22 can be either on the inside or outside of the tubular net 12 without departing from the spirit and scope of the present invention.

Due to the presence of the tubular net 12 which "encapsulates" the plaque 46 in the area of treatment 44, the struts of the primary stent 32 are not as susceptible of cutting into the plaque and breaking off pieces which could be released into the bloodstream. Rather, the tubular net 12 helps prevent the struts from cutting into the plaque. As a result, a primary stent can utilized which has larger cells or wider gaps between struts which can produce a much more flexible stent for primary stenting purposes. Additionally, by having larger gaps in the strut pattern, a stent having a much lower profile can be utilized in conjunction with the plaque-trapping device 10 to perform interventional procedures in small diameter blood vessels.

It should be appreciated that although the procedure shown in FIGS. 3–7 utilize a self-expanding stent 32, it is also possible to utilize a conventional stent which relies upon the application of a outward radial force to move the stent into its expanded condition within the artery. Additionally, while the expandable members 20 of the plaque-trapping device 10 shown in FIGS. 1–7 are made from a self-expanding material, and it is also possible to utilize other materials which are not self-expanding but also rely upon the application of an outward radial force, which can be delivered by the inflation of a balloon catheter, to place the expandable members into the expanded position.

The expandable members used in the present invention can be made from materials such as Nitinol, NiTi alloys, and other self-expanding materials. Alternatively, the expandable member could be made from a plastic material which can also self-expand upon deployment or can be deployable upon application of an outward radial force. Other suitable materials would include standard materials used for stents such as stainless steel, tantalum and polymeric materials, which usually are not selfexpanding. When formed from alloys such as Nitinol, the expandable member will rapidly expand radially outward to assume its preformed, expanded state. Alternate shaped memory materials that may be used to perform the expandable members include Stress-induced Martensite (SIM) alloys, which transform into martensite upon the application of stress, such as a compressive load, and return to their austenitic, preformed state when the stress is removed.

The restraining sheath which is utilized in conjunction with the delivery catheter must be of sufficient thickness to withstand the radially outward expansive force exerted by the primary stent and the plaque-trapping device. Suitable materials which can be utilized for the restraining sheath include materials such as polyolefin which has sufficient strength to hold the compressed stent and plaque-trapping device and has relatively low frictional characteristics to minimize any friction between the stent and the restraining sheath. The restraining sheath can be elastic, at least on the distal end, but not so elastic as to allow premature deployment of the safety net. Friction can be further reduced by applying a coat of silicon lubricant, such as Microglide®, manufactured by Advanced Cardiovascular Systems, Inc., Santa Clara, Calif., or hydrophylic substances to further reduce the amount of frictional buildup between the restraining sheath and inner member. The inner member can be manufactured as a continuous inner tubular member from a material such as low or medium molecular weight polyolefin, examples of which include TE, EVAc, EVA, and IONONERS. Any other plastically deformable materials or blended materials, including cross-link materials and composites, may also be suitable for use.

Referring now to FIGS. 8–11, another embodiment of a plaque-trapping device 52 is shown deployed into an artery 42 of a patient. In this particular embodiment of the present invention, the plaque-trapping device 10 includes a tubular net 12 having a proximal end 14 and a distal end 16 and an inner lumen 18 extending there through, but includes expandable members 54 which are formed from stent-like members, as opposed to single end rings as shown in the previous embodiment.

Figure 8:
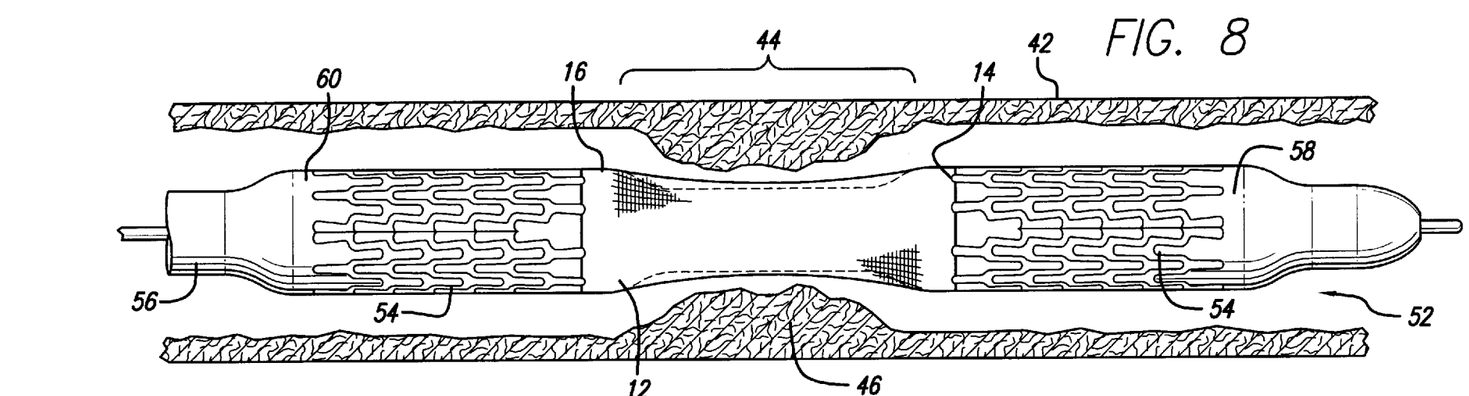
FIG. 8 is a side view of another embodiment of a plaque trapping device made in accordance with the present invention mounted on a balloon delivery catheter which is positioned within the atherosclerotic plaque site of a blood vessel.
Figure 9:
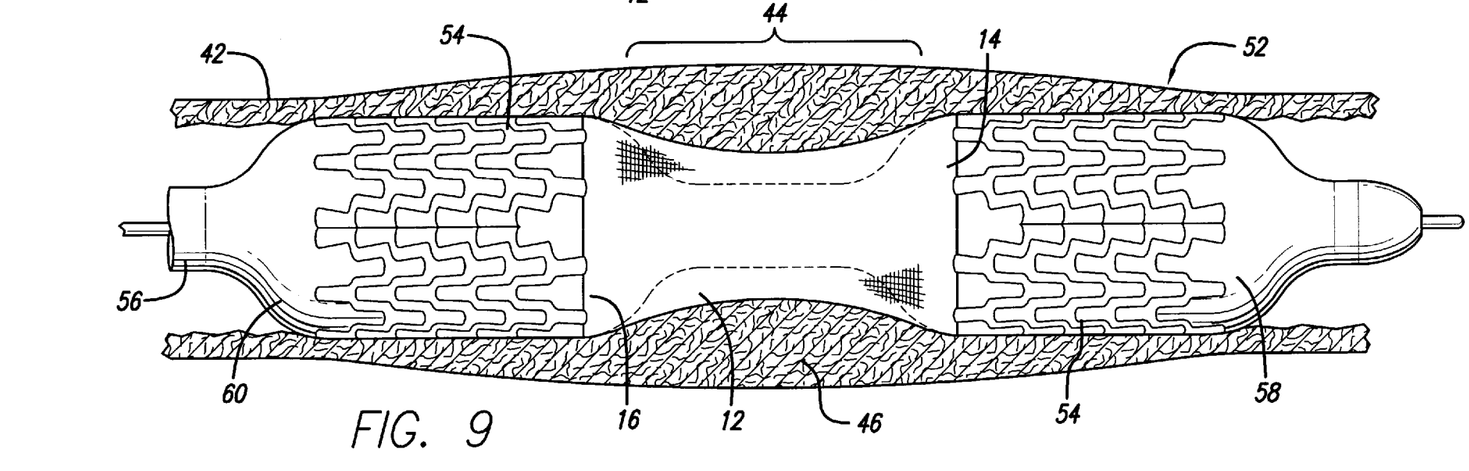
FIG. 9 is a side view of the plaque-trapping device of FIG. 8 as the balloon delivery catheter expands the expandable members located at the ends of the tubular net portion.

Referring now specifically to FIG. 8, this plaque-trapping device 52 is shown deployed into the area of treatment 44 such that the tubular net 12 is placed in position over the area of treatment 44 to encapsulate the plaque 46. A balloon catheter 56 is utilized in conjunction with this embodiment since this particular embodiment of the plaque-trapping device 52 utilizes conventional stents which must be deployed utilizing an outward radial force, such as that applied by the inflation of a balloon portion of a catheter. As can be seen better in FIG. 9, this balloon catheter 56 has a first balloon portion 58 and a second balloon portion 60 which form an overall "dog-bone" pattern. As a result, as the first and second balloon portions 58 and 60 are inflated, the expandable members 54 located on the proximal and distal ends 14 and 16 of the tubular net 12 are deployed into the expanded condition to contact the inner wall 48 of the artery 42. This securely implants the plaque-trapping device 52 into the area of treatment 44 to allow the physician to perform an interventional procedure in the area of treatment without the fear of breaking plaque for release into the bloodstream. Alternatively, the first balloon portion 58 would be inflated first to deploy the distal most expandable member 54. The same balloon portion 60 can then be inflated to expand the other expandable member 54 affixed to the proximal end 14 of the tubular net 12.

Figure 10:
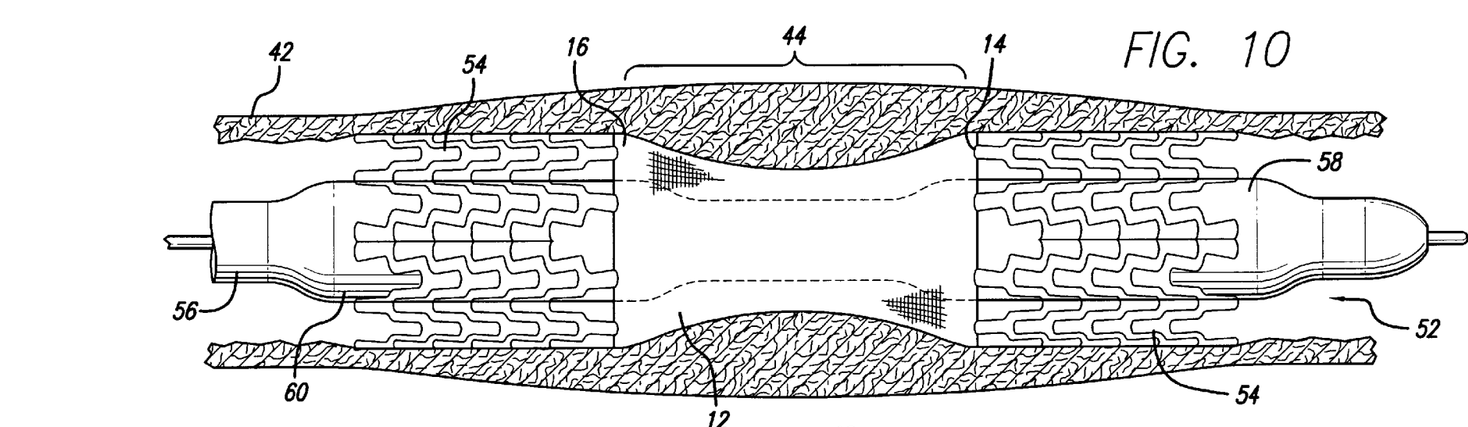
FIG. 10 is a side view of the plaque-trapping device of FIG. 9 wherein the balloon delivery catheter is contracted after the expandable members have been deployed within the blood vessel.
Figure 11:
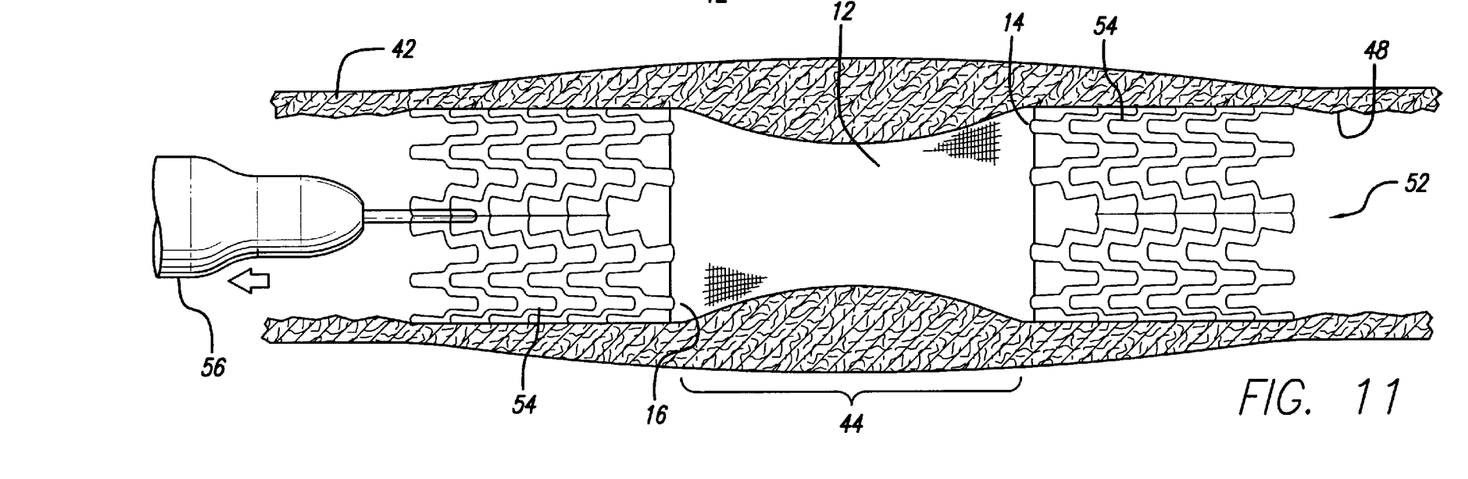
FIG. 11 is a side view of the plaque-trapping device of FIG. 10 wherein the balloon delivery catheter is being removed with the plaque-trapping device deployed against the atherosclerotic plaque site of the blood vessel.

Referring now to FIGS. 10 and 11, the balloon catheter 56 is first shown in FIG. 10 as the first balloon portion and second balloon portion 60 are deflated, resulting in the expandable members 54 remaining in place within the artery 42. Thereafter, the delivery catheter can be withdrawn from the area of treatment 44 by the physician by simply retracting the entire device along the guidewire 40, as is shown in FIG. 11. The plaque-trapping device 52 is now in position for the particular interventional device which will be performed to compress the plaque 46 in this area of treatment 44. An interventional device such as a self-expanding stent can be placed across the tubular net 12 to treat the lesion. A balloon expandable stent also can be used. The plaque-trapping device 52 should be placed across the lesion such that the stent which is to be placed into the area of treatment 44 does not make direct contact with the ends of the expandable members 54, to avoid stent compression.

It should also be appreciated that this plaque-trapping device 52 as shown in FIGS. 8–11 can also be made with expandable members 54 which are self-expanding. In such an embodiment, there is no need for a first and second balloon portion since an outward radial force is not needed to deploy the expandable members 54. Rather, the delivery catheter which could be utilized with a self-expanding plaque-trapping device 52 could utilize a restraining sheath as the one described above. The retraction of the restraining sheath would thus allow the expandable members 54 to be deployed into the unexpanded position within the artery 42.

In the embodiment of the plaque-trapping device which utilizes stents as the expandable members, stents may be an expandable tube with slots or other shaped apertures cut therein, or wire mesh, or a wire coil, or any other practical expanding device. Co-owned U.S. Pat. No. 5,514,154 to Lau et al., U.S. Pat. No. 5,569,295 to Lam, U.S. Pat. No. 5,591,197 to Orth et al., U.S. Pat. No. 5,603,721 to Lau et al., U.S. Pat. No. 5,649,952 to Lam, U.S. Pat. No. 5,728,158 to Lau et al., and U.S. Pat. No. 5,735,893 to Lau et al., describe suitable stents. The length of the stent used as an expandable member can be shorter that conventional stents as primary stenting of the stenosis is not the intended purpose of these expandable members. For this reason, the expandable member may be made from a "mini" stent which includes several cylindrical rings which form a shortened portion.

Figure 12:
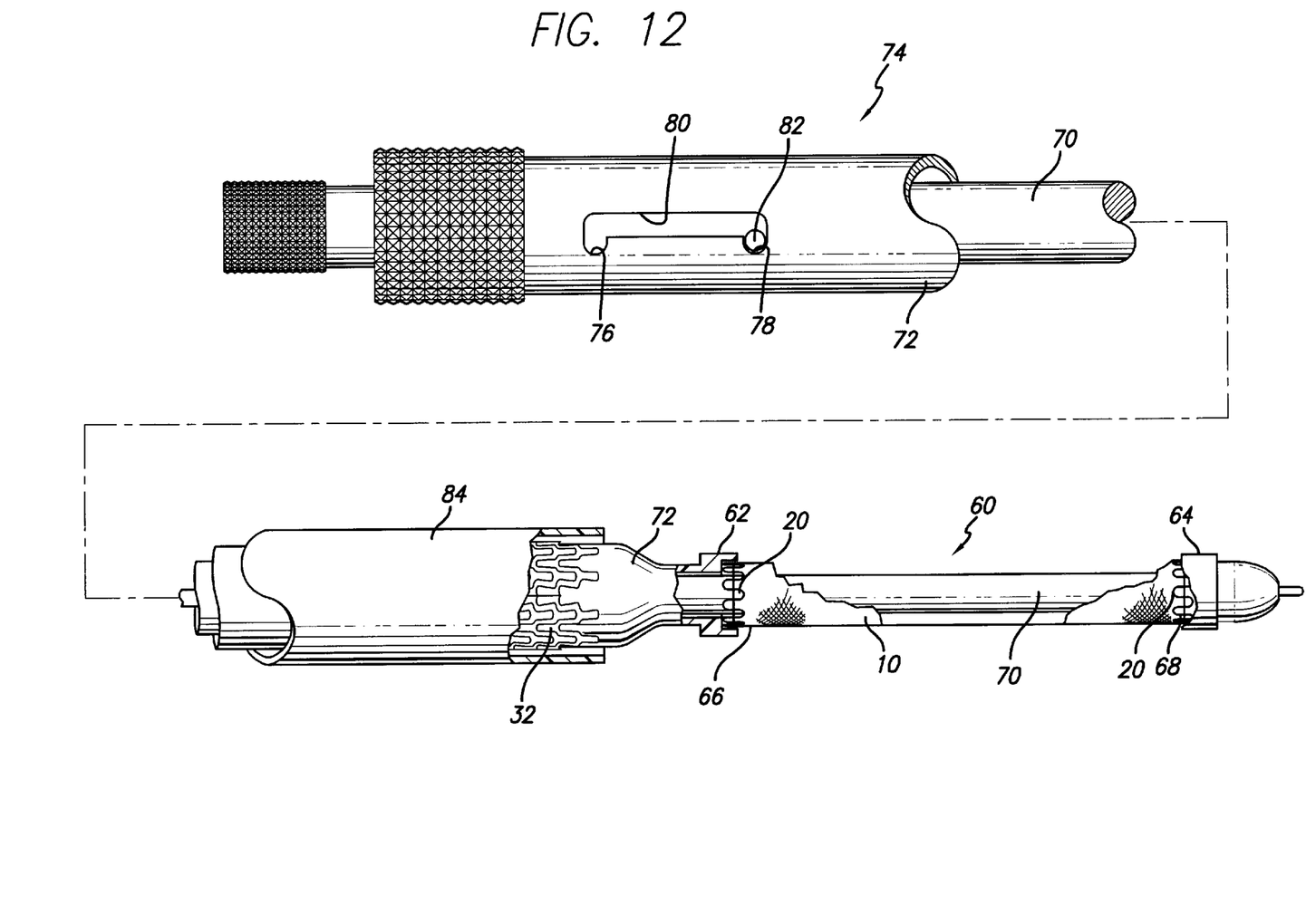
FIG. 12 is a side view of an alternative embodiment of a delivery catheter which can have an ultra-low profile to deliver a plaque-trapping device, such as the device shown in FIG. 1, into the patient's vasculature.
Figure 13:
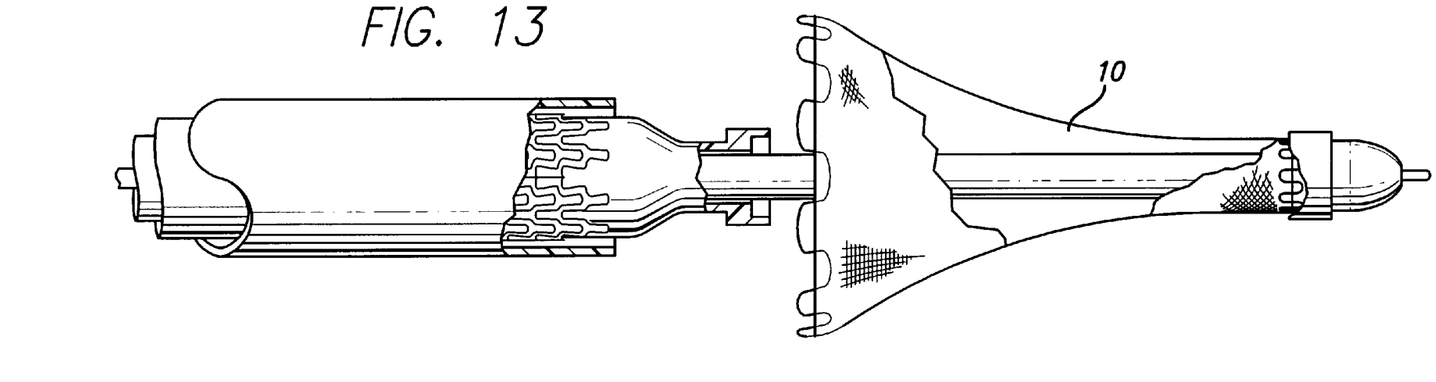
FIG. 13 is a side view of the delivery catheter of FIG. 12 and the plaque-trapping device as the plaque-trapping device is being partially deployed into its expanded position.
Figure 14:
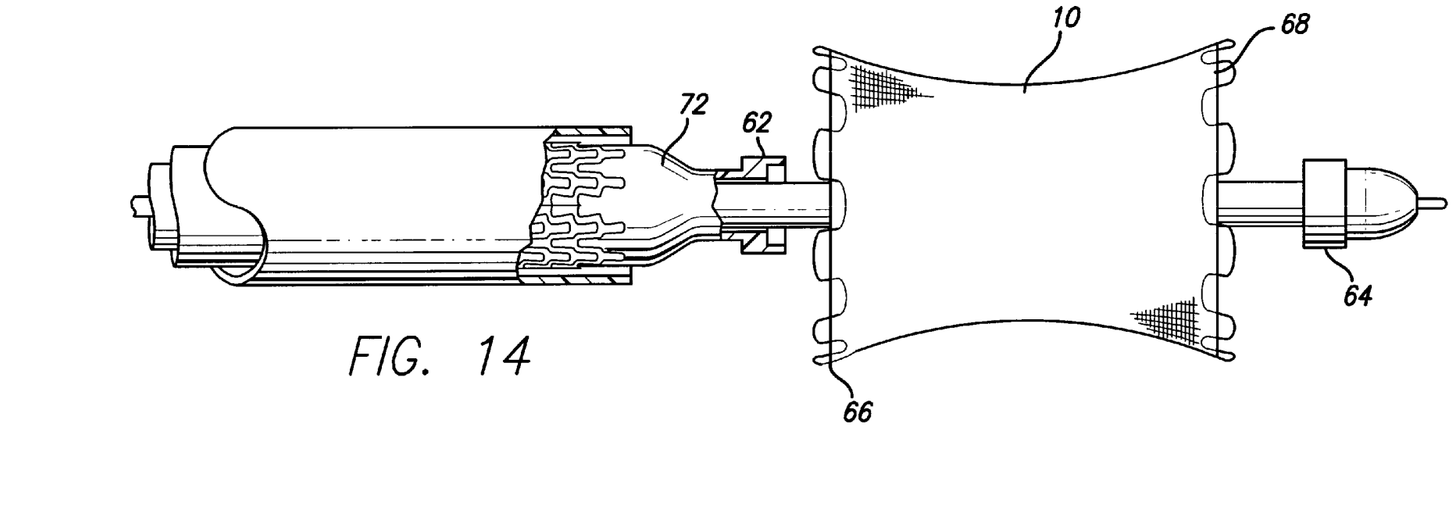
FIG. 14 is a side view of the delivery catheter of FIG. 12 and the plaque-trapping device wherein the plaque-trapping device has been deployed in its fully-expanded position.

Referring to FIGS. 12–14, an alternative delivery catheter 60 for delivering a plaque-trapping device 10 is shown. This particular delivery catheter 60 provides an ultra-low profile which allows the device 10 to be steered into more distal anatomy and across tighter lesions. In this particular version, the plaque-trapping device 10 is not encased by a restraining sheath, but rather, is delivered on a delivery catheter 60 which utilizes a pair of restraining elements 62 and 64 that retain the ends 66 and 68 of the plaque-trapping device 10 until the device 10 is ready to be deployed. As can be seen in FIG. 12, the delivery catheter 60 includes an inner member 70 to which the proximal restraining element 68 is attached. The other restraining element 66 is affixed to the end of the inner member 72 which delivers the stent 32 to the area of treatment. Each of the restraining elements 62 and 64 basically comprises a flap of material which extends over the inner shaft 70 and has a space into which the ends 66 and 68 of the plaque-trapping device 10 is mounted. The restraining elements 62 and 64 maintain the end rings 20 of the device 10 in the compressed or collapsed position until the restraining elements are retracted to allow the plaque-trapping device 10 to deploy. A simple locking mechanism 74 can be utilized to maintain the restraining element 62 and 64 in a set position to hold and maintain the plaque-trapping device 10 in its compressed position until the device is ready to be deployed. The locking mechanism 74 includes a first locking position 76 and a second locking position 78 which are formed on an elongated groove or slot 80 which is formed on the inner member 72. A raised dimple 82 on the inner member 70 can be used to move the respective elements between the first locking position 76 and second locking position 78.

Referring now to FIGS. 13 and 14, once the device 10 is ready to be deployed, the physician merely moves the inner member 70 forward from the first locking position 76 to the second locking position 78 in order to move the restraining elements 62 and 64 away from each other. In this manner, the ends 66 and 68 of the plaque-trapping device 10 move out from the recess of the restraining element 62 and 64 to allow the plaque-trapping device 10 to move to a fully-expanded position. Thereafter, the delivery catheter can be utilized to deploy the stent 32 into the area of treatment by retracting the restraining sheath 84 used in the deployment of the stent 32. Thereafter, the entire delivery catheter can be withdrawn from the patient's vasculature after the stent 32 has been deployed.

The advantages of utilizing this particular delivery catheter eliminates the need for a restraining sheath on the end of the catheter to maintain the plaque-trapping device 10 in its compressed position. Thus, a lower profile is obtainable which helps when deploying the system into distal anatomy and through tight lesions. The restraining elements 62 and 64 can be made from polymeric materials which have sufficient strength to hold the expandable members 20 in their collapsed position until the device 10 is ready to be deployed. It should be appreciated that both ends of the plaque-trapping device 10 may not immediately withdraw from the restraining elements simultaneously, and that one end of the plaque-trapping device 10 may not be released from its restraining element until after the other end of the device 10 has been deployed, as is shown in the sequence of the drawings shown in FIGS. 13 and 14.

In view of the foregoing, it is apparent that the system and method of the present invention greatly enhance the safety of angioplasty procedures by significantly minimizing the risk associated with friable plaque deposits breaking away from the vascular wall and migrating into the patient's bloodstream to form emboli and potential life-threatening injury to the patient. Further modification of the improvements may be made to the system and device disclosed herein without departing from the spirit and scope of the present invention. Accordingly, it is not intended that the invention be limited, except as by the appended claims.

What is claimed:

1. A system for treating an area of plaque in a blood vessel and minimizing the possibility of emboli from the plaque entering the bloodstream, comprising:

a plaque-trapping device including a permanently implantable tubular net having proximal and distal ends and an inner lumen formed therein, said tubular net being made from a flexible, blood permeable and biocompatible material with an expandable member attached to each of said proximal and distal ends of said tubular net which is capable of expanding from a collapsed to an expanded condition to contact the wall of the blood vessel to maintain the tubular net over the area of plaque;

an implantable stent expandable from a contracted to an expanded condition and adapted for placement within the inner lumen of said tubular net for compressing the plaque when deployed into the expanded condition; and a delivery catheter having an inner member with a first region for mounting said implantable stent when in the contracted condition and a second region for mounting said plaque-trapping device when in the collapsed condition, along with a retractable restraining sheath overlying said inner member adapted for axial movement with respect to said inner member for deploying said plaque-trapping device and stent in the blood vessel.

2. The system of claim 1, wherein said expandable members of said plaque-trapping device are made from self-expanding material.

3. The system of claim 2, wherein said implantable stent is made from a self-expanding material.

4. The system of claim 3, wherein said first and second mounting regions of said delivery catheter have a substantially cylindrical shape and the diameter of said second mounting region is smaller then the diameter of said first mounting region.

5. The system of claim 4, wherein said plaque-trapping device has a longitudinal length and said implantable stent has a longitudinal length with the longitudinal length of said plaque-trapping device being less than the longitudinal length of said implantable stent.

6. The system of claim 5, wherein said plaque-trapping device includes a plurality of struts attached to each of said expandable members to maintain a set longitudinal length between each of said expandable members.

* * * * *